United States Patent
Matthijs et al.

[11] Patent Number: 5,769,808
[45] Date of Patent: Jun. 23, 1998

[54] WRIST SUPPORT BAND

[76] Inventors: Omer C. Matthijs; Valerie A. Phelps, both of 1980 N. Box Canyon Pl., Tucson, Ariz. 85745

[21] Appl. No.: 756,889

[22] Filed: Dec. 2, 1996

[51] Int. Cl.[6] .................................................... A61F 5/00
[52] U.S. Cl. .............................................. 602/64; 602/63
[58] Field of Search .................................. 602/60–64, 5; 128/856, 878, 879

[56] References Cited

U.S. PATENT DOCUMENTS

| | | | |
|---|---|---|---|
| 2,068,173 | 1/1937 | Galves | 602/64 |
| 3,710,790 | 1/1973 | Lemon | 602/64 X |
| 3,877,426 | 4/1975 | Nirschl | 602/62 |
| 4,702,234 | 10/1987 | Huntjens | 602/21 |
| 5,135,473 | 8/1992 | Epler et al. | 602/62 |
| 5,267,943 | 12/1993 | Dancyger | 605/5 |
| 5,306,229 | 4/1994 | Brandt et al. | 602/64 X |
| 5,368,550 | 11/1994 | Sisley | 602/64 X |
| 5,404,591 | 4/1995 | Brinnand et al. | 2/161.6 X |
| 5,469,900 | 11/1995 | Kline | 128/879 X |
| 5,513,657 | 5/1996 | Nelson | 128/879 |

FOREIGN PATENT DOCUMENTS

| | | | |
|---|---|---|---|
| 602317 | 6/1994 | European Pat. Off. | 602/26 |
| 2607384 | 6/1988 | France | 602/63 |
| 4238610 | 5/1994 | Germany | 602/21 |

*Primary Examiner*—Richard J. Apley
*Assistant Examiner*—Denise Pothier
*Attorney, Agent, or Firm*—Palmatier, Sjoquist, Voigt & Christensen, P.A.

[57] ABSTRACT

A wrist support band for use in the treatment of wrist ailments. The wrist support band provides support to the wrist while at the same time allows mobility of the wrist. The wrist support band includes an elastic sleeve that contains a flexible mold support. The mold support incorporates two elongated protuberances and a central recess intermediate the protuberances. The sleeve is slid over the hand and wrist until the elongated protuberances are proximate the wrist's proximal carpal row. At least one strap is wrapped about the sleeve to hold the sleeve and mold support in position firmly against the wrist. The interior of the sleeve may also be equipped with an anti-slip patch to prevent the sleeve from sliding up and down the wrist or forearm.

20 Claims, 2 Drawing Sheets

WRIST SUPPORT BAND

BACKGROUND OF THE INVENTION

A great number of the population suffer from ailments that affect movement of the wrist. These ailments include: non-dissociative dorsiflexion intercalated segment instability or DISI; slight to moderate palmar translocations of the wrist, as a result of generalized hypermobility or post-macrotraumatic conditions (distal radial fractures with and without malalignment); status after luxation-fractures of the wrist; carpal tunnel syndrome as a result of carpal instability; ulno-carpal instability as a result of generalized hypermobility or post macrotraumatic conditions; triangular fibrocartilaginous complex lesions; ulnar tunnel syndrome as a result of ulnocarpal palmar translocation; and others.

To accommodate these wrist ailments, a number of support systems for the wrist have been developed. Many supports offer good stability, but their designs inhibit easy mobility of the wrist. The decreased mobility results in decreased compliance of the patient in wearing the support system. Remodeling of connective tissue is a slow process thus, decreased compliance in wearing a wrist support system can extend treatment for extra months, years or may even result in completely ineffectual treatment. As such, there is a tremendous need for a wrist support system that allows some mobility in the wrist. However, currently there are no wrist supports known that offer stability to the kinematical complex of the wrist while at the same time allow an adequate amount of mobility of the wrist.

SUMMARY OF THE INVENTION

The wrist support band may be used in the treatment of wrist ailments. The use of the wrist support band provides support to the wrist while at the same time allows mobility of the wrist. The wrist support band includes an elastic sleeve that contains an interior flexible mold support. The mold support incorporates two elongated tapered protuberances and a central recess intermediate the protuberances. The sleeve is slid over the hand and wrist until the elongated protuberances are proximate the wrist's proximal carpal row. At least one strap is wrapped about the sleeve to hold the sleeve and mold support in position firmly against the wrist. A securement means is provided to secure the strap about the sleeve. The interior of the sleeve may also be equipped with an anti-slip patch to prevent the sleeve from sliding up and down the wrist or forearm.

It is a principal object of the present invention to provide a new and improved wrist support band of relatively simple and inexpensive design, construction and operation, which is safe and durable and which may be used by an individual in treating wrist ailments.

Another principal object of the present invention is to supply stability to the kinematical complex of the wrist while at the same time allowing for an adequate amount of mobility in the wrist by controlling movement patterns of only the proximal carpal row.

A feature of the present invention is a sleeve that can be slid over the hand and wrist.

Another feature of the present invention is a mold support that has two elongated protuberances and a central recess intermediate the elongated protuberances. The mold support is attached to the interior of the sleeve such that when the sleeve is slid over the hand and wrist the elongated protuberances are proximate the wrist's proximal carpal row.

Still another feature of the present invention is that the elongated protuberances of the mold support extend from the front end of the mold support to the rear end of the mold support and taper from approximately the midpoint of the mold support to the rear end. The tapering of the protuberances provides extra comfort to the user, as along the tapered portion of the protuberances pressure against the wrist is decreased. Furthermore, the tapering allows more mobility of the rear end of the wrist (the area toward the forearm).

Still another feature of the present invention is at least one strap that may be wrapped about the exterior of the sleeve to hold the mold support, its protuberances and the interior of the sleeve in position firmly against the wrist.

Still another feature of the invention is a securement means that secures the strap about the sleeve.

Still another feature of the invention is an anti-slip patch that can be provided on the interior of the sleeve to prevent the sleeve and mold support from sliding up and down the forearm or wrist.

DETAILED DESCRIPTION OF THE PREFERRED EMBODIMENT

Figure 1:
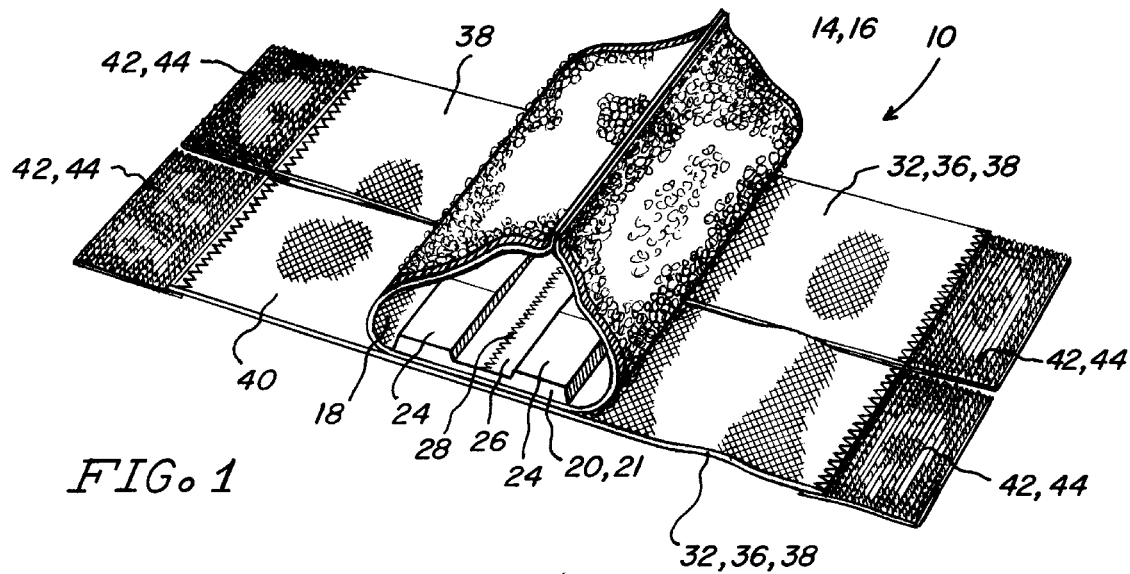
FIG. 1 is a front perspective view of the wrist support band.

One form of the invention is illustrated and described herein. The wrist support is enumerated as item 10 and generally comprises a sleeve 14, a mold support 20, an anti-slip patch 30, two straps 32 and a securement means 42.

Figure 2:
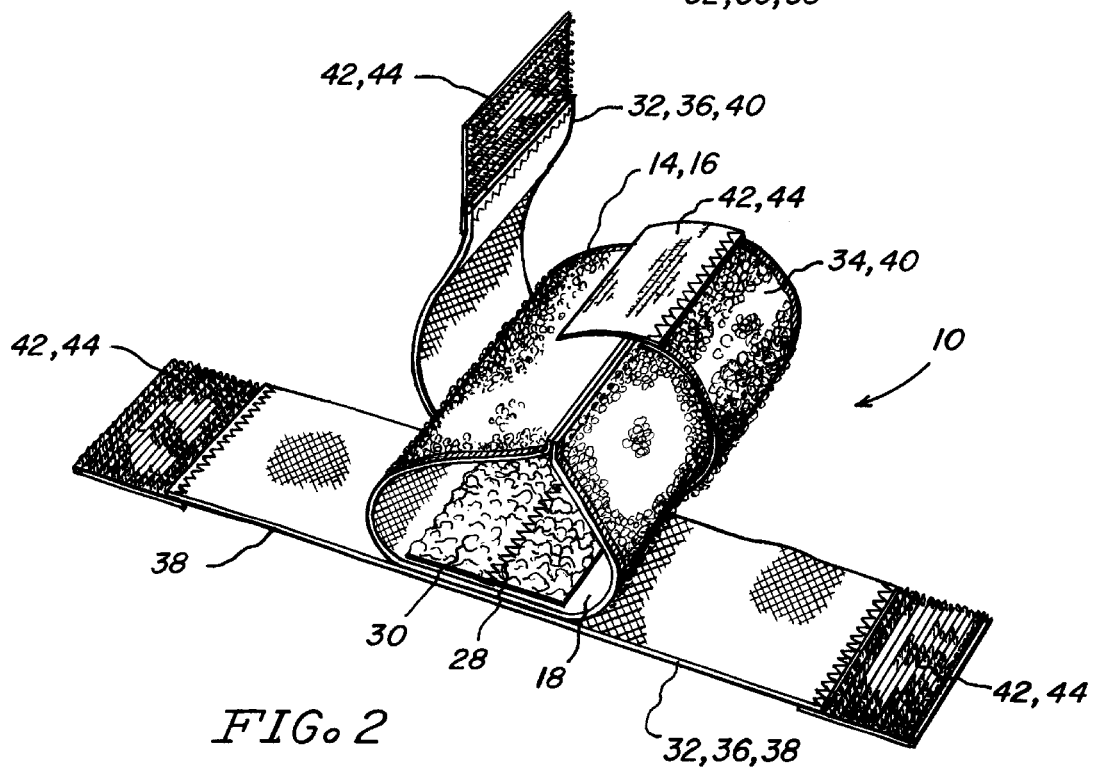
FIG. 2 is a rear perspective view of the wrist support band with the proximal bands wrapped about the sleeve.
Figure 3:
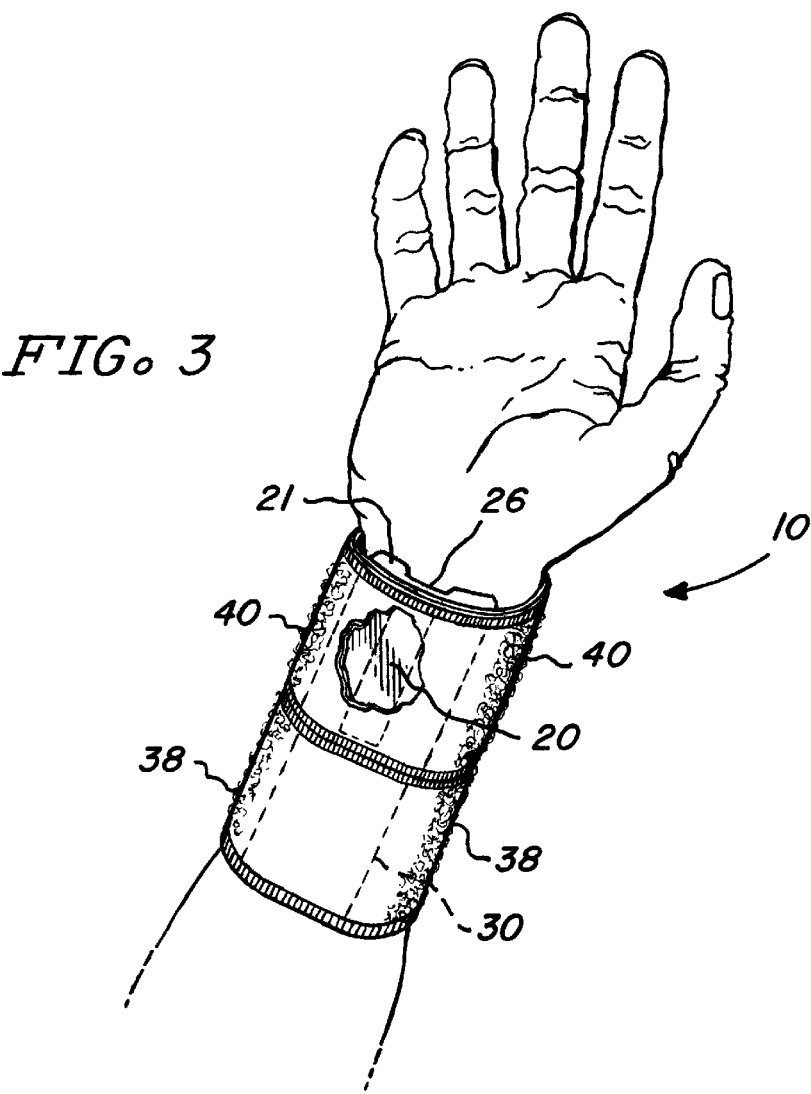
FIG. 3 is an environmental view of the wrist support band as it is applied to a wrist, the molded support and anti-slip patch are shown in phantom.

The sleeve 14 is of a tubular shape and is made of a soft, breathable and washable elastic fabric that allows the sleeve to be slid over the hand and wrist of an individual (FIGS. 1 and 2). The sleeve 14 can be made in a number of diameters to accommodate various users who naturally have differing wrist circumferences. The exterior 16 of the sleeve 14 incorporates a loop material while the interior 18 of the sleeve 14 is generally a soft, fairly smooth surface.

Figure 4:
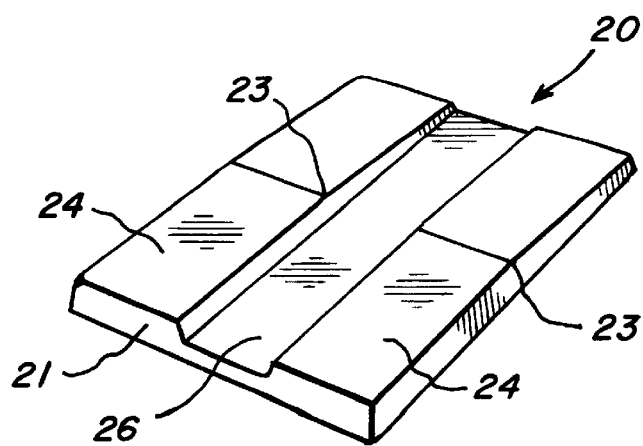
FIG. 4 is a perspective view of the mold support.

The mold support 20 is generally square or rectangular in shape and is made of a soft, flexible rubber or rubber-like material. The mold support 20 has a front end 21, a rear end 22, a midpoint 23, two elongated protuberances 24 and a central recess 26 intermediate the elongated protuberances 24. The elongated protuberances 24 extend from the front end 21 of the mold support 20 to the rear end 22. However, the protuberances 24 taper from approximately the midpoint 23 of the mold support to the rear end 22 of the mold support (FIG. 4). The elongated protuberances 24 themselves may be of a rounded or rectangular cross section. The mold support 20 is attached to the sleeve with a nylon-like thread 28, the thread 28 running the length of the central recess 26. While a nylon-like thread is appropriate and most durable, other types of attachment means may also be used such as adhesives, cotton thread, plastic thread, nylon or plastic rivets.

Located adjacent the mold support 20 within the interior 18 of the sleeve 14 is an anti-slip patch 30 (FIG.'s 1–3). The anti-slip patch 30 is a thin, rubber or rubber-like material attached to the sleeve 14 with a nylon-like thread 28, as described above. Once again, alternate attachment means such as those described above may be used. The anti-slip patch helps to prevent the sleeve 14 from sliding up or down the user's arm/wrist; it is especially helpful when the wrist support band 10 is worn for long periods of time or when the user's wrist is active with twisting and turning motions.

Attached to the exterior 16 of the sleeve 14 are two elongated straps 32 of soft, breathable and washable elastic fabric identical to the fabric used for the sleeve 14 (FIG.'s 1 and 2). Each of the straps 32 is attached with nylon-like thread 28 to the sleeve 14. It is advantageous to use only one length of the nylon-like thread 28 to attach all components including the mold support 20, anti-slip patch 30 and the elongated straps 32; numerous layers of thread, if used, may bunch and protrude into the interior of the sleeve 14 causing discomfort to the user. Similar to the sleeve 14, the elongated straps 32 have an exterior 34 that incorporates a loop material while the interior 36 of the elongated straps 32 is generally soft and fairly smooth. The first strap 32 when sewn through its center for attachment to the sleeve 14 serves to form two proximal bands 38 while the second serves to form two distal bands 40 (FIG.'s 1–3). Note that the combined width of the straps 32 is approximately equal to the width of the sleeve.

Located at each end of the proximal bands 38 and distal bands 40 is a securement means 42. The securement means 42 is generally an affixation member 44 incorporating hook material that is engageable with the loop material of the sleeve 14 and bands 38, 40 (FIG.'s 1 and 2). Alternatively, the securement means 42 may comprise hooks, snaps, tape or butterfly fasteners.

The use of the wrist support band 10 will now be addressed. The initial application of the wrist support band 10 should always be under the supervision of a professional health care provider. To apply the wrist support band 10, the sleeve 14 is pulled over the hand onto the forearm so that the pole of the scaphoid and the pisiform are covered by the sleeve 14. The two protuberances 24 of the mold support 20 should rest against these two bony structures, the anti-slip patch 30 should be below or behind the mold support 20 on a portion of wrist or upper forearm. Next, with the forearm supinated, thumb clasped in hand and wrist in ulnar deviation, the proximal bands 38 are applied by pulling and wrapping the bands 38 firmly about the wrist/forearm and engaging the hook material of the affixation member 44 to the loop material of the sleeve 14 or proximal band 38 as appropriate.

Finally, care should be taken in applying the distal bands 40. In most instabilities (DISI), the distal bands 40 should be applied with the wrist still ulnarly deviated and slightly extended. However, in instances of volar translocation of the entire proximal carpal row or of only one ulnar column, dorsal realignment should be ensured before applying the distal bands 40. Actual application of the distal bands 40 is completed by pulling and wrapping the bands 40 firmly about the wrist and engaging the hook material of the affixation member 44 to the loop material of the sleeve 14 or distal band 40 as appropriate.

The wrist support band 10 should not be used to cover open wounds or local skin irritations and should not be used on individuals with vascular problems that could lead to the inability of the individual to feel too much pressure from the support band.

The present invention may be embodied in other specific forms without departing from the spirit or essential attributes thereof, therefore, the illustrated embodiment should be considered in all respects as illustrative and not restrictive, reference being made to the appended claims rather than to the foregoing description to indicate the scope of the invention.

What is claimed is:

1. A wrist support band for surrounding a wrist having a proximal carpal row, and supporting movement of the wrist, said wrist support band comprising:
    (a) a sleeve having an interior and an exterior, said sleeve adapted to slide over an individual's hand and wrist;
    (b) a flexible mold support attached to said interior of said sleeve, said flexible mold support having two elongated protuberances and a central recess intermediate said two elongated protuberances, said two elongated protuberances positionable proximate the wrist's proximal carpal row when said sleeve is slid over the wrist;
    (c) at least one strap about said exterior of said sleeve to hold said interior of said sleeve and said mold support in position proximate the wrist and the wrist's proximal carpal row; and
    (d) securement means for securing said strap about said sleeve.

2. The wrist support band of claim 1, further comprising an anti-slip patch, said anti-slip patch attached to said interior of said sleeve.

3. The wrist support band of claim 1, wherein said at least one strap further comprises two straps.

4. The wrist support band of claim 1, wherein said sleeve is made of a elastic fabric.

5. The wrist support band of claim 1, wherein said exterior of said sleeve comprises a loop material for engagement to said securement means.

6. The wrist support band of claim 1, wherein said securement means comprises an affixation member comprising hook material.

7. The wrist support band of claim 1, wherein said strap comprises a loop material for engagement to said securement means.

8. The wrist support band of claim 1, wherein said flexible mold support has a front end, a midpoint and a rear end, said elongated protuberances extending from said front end to said rear end, said elongated protuberances tapering from approximately said midpoint to said rear end.

9. A wrist support band for surrounding a wrist and supporting movement of the wrist, said wrist support band comprising:
    (a) a sleeve having an interior and an exterior, said sleeve adapted to slide over the wrist, the wrist having a proximal carpal row;
    (b) a flexible mold support attached to said interior of said sleeve, said flexible mold support having two elongated protuberances and a central recess intermediate said two elongated protuberances, said two elongated protuberances proximate the wrist's proximal carpal row when said sleeve is positioned over the wrist;
    (c) an anti-slip patch attached to said interior of said sleeve;
    (d) two straps, said two straps wrapped about said exterior of said sleeve to hold said sleeve and said flexible mold support in position proximate the wrist and the proximal carpal row; and
    (e) securement means for securing said two straps about said sleeve.

10. The wrist support band of claim 9, wherein said flexible mold support has a front end, a midpoint and a rear end, said two elongated protuberances extending from said front end to said rear end, said elongated protuberances tapering from approximately said midpoint to said rear end.

11. The wrist support band of claim 9, wherein said sleeve is made of elastic fabric.

12. The wrist support band of claim 9, wherein said exterior of said sleeve comprises a loop material for engagement to said securement means.

13. The wrist support band of claim 9, wherein said securement means comprises an affixation member comprising hook material.

14. The wrist support band of claim 9, wherein said sleeve has a defined width, said two straps each have a defined width, and the combination of said straps' defined width is approximately equal to said sleeve's defined width.

15. The wrist support band of claim 9, wherein said flexible mold support is made of a rubber or rubber-like material.

16. A wrist support band for surrounding a wrist and supporting movement of the wrist, said wrist support band comprising:

(a) an elastic sleeve having an interior and an exterior, said elastic sleeve adapted to slide over an individual's hand and wrist, the wrist having a proximal carpal row;

(b) a flexible mold support attached to said interior of said elastic sleeve, said mold support having a front end, a midpoint, a rear end, two elongated protuberances and a central recess intermediate said elongated protuberances, said elongated protuberances extending from said front end to said rear end, said elongated protuberances tapering from approximately said midpoint to said rear end, said elongated protuberances proximate the wrist's proximal carpal row when said elastic sleeve is slid over the individual's hand and wrist;

(c) an anti-slip patch attached to said interior of said elastic sleeve, said anti-slip patch adjacent said bottom end of said flexible mold support;

(d) two elastic straps, said two elastic straps attached to said elastic sleeve, said two elastic straps wrapped about said exterior of said elastic sleeve to hold said elastic sleeve, said flexible mold support and said anti-slip patch in position against the wrist; and (e) securement means for securing said two elastic straps about said elastic sleeve.

17. The wrist support band of claim 16, wherein said elastic sleeve has a defined width, said two elastic straps each have a defined width, and the combination of said two elastic straps' defined width is approximately equal to said sleeve's defined width.

18. The wrist support band of claim 16, wherein said exterior of said elastic sleeve comprises a loop material for engagement to said securement means.

19. The wrist support band of claim 16, wherein said securement means comprises an affixation member comprising hook material.

20. The wrist support band of claim 16, wherein said elastic straps comprise a loop material for engagement to said securement means.

* * * * *